(12) United States Patent
Rutenberg et al.

(10) Patent No.: US 9,119,865 B2
(45) Date of Patent: Sep. 1, 2015

(54) COMPOSITIONS AND METHODS FOR ALLEVIATING SYMPTOMS ASSOCIATED WITH PREMENSTRUAL SYNDROME AND PREMENSTRUAL DYSPHORIC DISORDER

(71) Applicant: Lipogen Ltd., Haifa (IL)

(72) Inventors: David Rutenberg, Haifa (IL); Rina Perry Faierwerger, Moshav Bat Shlomo (IL)

(73) Assignee: Lipogen Ltd., Haifa (IL)

( * ) Notice: Subject to any disclaimer, the term of this patent is extended or adjusted under 35 U.S.C. 154(b) by 315 days.

(21) Appl. No.: 13/773,653

(22) Filed: Feb. 22, 2013

(65) Prior Publication Data

US 2013/0171269 A1    Jul. 4, 2013

Related U.S. Application Data

(63) Continuation-in-part of application No. 12/606,975, filed on Oct. 27, 2009, now Pat. No. 8,399,432.

(51) Int. Cl.

| | |
|---|---|
| *A61K 31/66* | (2006.01) |
| *A61K 31/661* | (2006.01) |
| *A61K 33/06* | (2006.01) |
| *A61K 31/225* | (2006.01) |
| *A61K 31/685* | (2006.01) |
| *A23L 1/30* | (2006.01) |
| *A23L 1/304* | (2006.01) |
| *A61K 33/08* | (2006.01) |

(52) U.S. Cl.
CPC .............. *A61K 31/661* (2013.01); *A23L 1/304* (2013.01); *A23L 1/3008* (2013.01); *A61K 31/225* (2013.01); *A61K 31/685* (2013.01); *A61K 33/06* (2013.01); *A61K 33/08* (2013.01)

(58) Field of Classification Search
CPC .... A61K 33/06; A61K 31/225; A61K 31/685
USPC ......................................................... 514/121
See application file for complete search history.

(56) References Cited

U.S. PATENT DOCUMENTS 6,410,622 B1 * 6/2002 Endres ........................ 524/189

* cited by examiner

*Primary Examiner* — San-Ming Hui
(74) *Attorney, Agent, or Firm* — Reuven K. Mouallem; FlashPoint IP Ltd.

(57) ABSTRACT

The present invention discloses pharmaceutical/nutritional compositions and methods for alleviating symptoms associated with premenstrual syndrome (PMS) and premenstrual dysphoric disorder (PMDD). The pharmaceutical/nutritional compositions include at least 2% (w/w) phosphatidyl-L-serine, or salts thereof, out of a total effective composition, as a first effective ingredient; and a suitable amount of at least one bio-available form of magnesium as a second effective ingredient. Preferably, the bio-available form of magnesium is magnesium oxide, magnesium citrate, magnesium hydroxide, magnesium stearate, or a magnesium salt of the phosphatidyl-L-serine. Preferably, the composition further includes a pharmaceutical or nutritional excipient. Preferably, the total effective composition is administrable in a multi-part regimen. Preferably, the total effective composition is administrable by intravenous or oral delivery. Preferably, the pharmaceutical/nutritional composition further includes at least 2% (w/w) phosphatidic acid, or salts thereof, out of the total effective composition, as a first effective ingredient.

6 Claims, No Drawings

COMPOSITIONS AND METHODS FOR ALLEVIATING SYMPTOMS ASSOCIATED WITH PREMENSTRUAL SYNDROME AND PREMENSTRUAL DYSPHORIC DISORDER

CROSS REFERENCE TO RELATED APPLICATIONS

This patent application is a continuation-in-part (CIP) of, and claims priority to, U.S. patent application Ser. No. 12/606,975, filed on Oct. 27, 2009, which is hereby incorporated by reference in its entirety.

FIELD AND BACKGROUND OF THE INVENTION

The present invention relates to compositions and methods for alleviating symptoms associated with premenstrual syndrome (PMS) and premenstrual dysphoric disorder (PMDD).

The U.S. Department of Health and Human Services, Office on Women's Health, summarizes that PMS is a group of symptoms linked to the menstrual cycle. PMS symptoms occur in the week or two weeks prior to menstruation. PMS may be just a monthly bother, or it may be so severe that it makes it hard to even get through the day. Up to 80% of women experience some symptoms of PMS. The causes of PMS are not clear, and are linked to hormonal changes during the menstrual cycle. Stress and emotional problems do not seem to cause PMS.

The inclusion of PMDD in the fifth edition of the Diagnostic and Statistical Manual of Mental Disorders (DSM-5, due for release in 2013) is indicative of the dynamic and controversial attitude toward PMDD as a full-fledged disorder within the scientific community. PMDD was previously considered to be synonymous with PMS. The scientific community later differentiated PMDD as a subset of symptoms associated with PMS, and more recently as a specific type of occurrence of PMS. However, PMDD is not viewed as a unique disorder globally, particularly in Europe.

In a scientific article by Epperson et al. (*Am J Psychiatry*, 2012 May; 169(5):465-75) entitled, "Premenstrual Dysphoric Disorder: Evidence for a New Category for DSM-5," the abstract states, "Based on thorough review and lengthy discussion, the work group proposed that the information on the diagnosis, treatment, and validation of the disorder has matured sufficiently for it to qualify as a full category in DSM-5."

This clearly suggests a shift has occurred in the state-of-the-art understanding of PMDD vis-à-vis PMS. That is, while PMDD was once considered to be synonymous with PMS, it later came to be commonly understood as an offshoot of PMS, exhibiting a similar rubric of symptoms associated with menstruation. The inclusion of PMDD in the DSM-5 further validates the recognition of such a "subset" disorder as PMDD as a stand-alone mental disorder.

It would be desirable to have compositions and methods for alleviating symptoms associated with PMS and PMDD.

SUMMARY OF THE INVENTION

It is the purpose of the present invention to provide compositions and methods for alleviating symptoms associated with PMS and PMDD.

Furthermore, it is noted that the term "exemplary" is used herein to refer to examples of embodiments and/or implementations, and is not meant to necessarily convey a more-desirable use-case. Similarly, the term "preferred" is used herein to refer to an example out of an assortment of contemplated embodiments and/or implementations, and is not meant to necessarily convey a more-desirable use-case. Therefore, it is understood from the above that "exemplary" and "preferred" may be applied herein to multiple embodiments and/or implementations.

Embodiments of the present invention provide compositions and methods, for decreasing PMS and PMDD symptoms, including phosphatidyl-L-serine and/or phosphatidic acid and a bio-available form of magnesium. Such compositions are administrable via intravenous or oral administration. Such compositions can also include other excipients (e.g., additional phospholipids, lyso-phospholipids, sugars, and proteins) to prepare capsules, tablets, and granules with improved handling and shelf life. Because of the absence of any safety problem, such compositions can be blended into daily foods and beverages, either in powder or liquid form, or as a hydrogenated substance for use in decreasing PMS/PMDD symptoms. Embodiments of the present invention further provide compositions and methods including phosphatidic acid.

Therefore, according to the present invention, there is provided for the first time a pharmaceutical/nutritional composition for alleviating symptoms associated with premenstrual syndrome (PMS) and premenstrual dysphoric disorder (PMDD), the pharmaceutical/nutritional composition including: (a) at least 2% (w/w) phosphatidyl-L-serine, or salts thereof, out of a total effective composition, as a first effective ingredient; and (b) a suitable amount of at least one bio-available form of magnesium as a second effective ingredient.

Preferably, at least one bio-available form is selected from the group consisting of: magnesium oxide, magnesium citrate, magnesium hydroxide, and magnesium stearate.

Preferably, at least one bio-available form is a magnesium salt of the phosphatidyl-L-serine.

Preferably, the pharmaceutical/nutritional composition further includes: (c) a pharmaceutical excipient.

Preferably, the pharmaceutical/nutritional composition further includes: (c) a nutritional excipient.

Preferably, the total effective composition is administrable in a multi-part regimen.

Preferably, the total effective composition is administrable by at least one delivery method selected from the group consisting of: oral delivery and intravenous delivery.

According to the present invention, there is provided for the first time a pharmaceutical/nutritional composition for alleviating symptoms associated with premenstrual syndrome (PMS) and premenstrual dysphoric disorder (PMDD), the pharmaceutical/nutritional composition including: (a) at least 2% (w/w) phosphatidic acid, or salts thereof, out of the total effective composition, as a first effective ingredient; and (b) a suitable amount of at least one bio-available form of magnesium as a second effective ingredient.

Preferably, at least one bio-available form is selected from the group consisting of: magnesium oxide, magnesium citrate, magnesium hydroxide, and magnesium stearate.

Preferably, at least one bio-available form is a magnesium salt of the phosphatidic acid.

Preferably, the pharmaceutical/nutritional composition further includes: (c) a pharmaceutical excipient.

Preferably, the pharmaceutical/nutritional composition further includes: (c) a nutritional excipient.

Preferably, the total effective composition is administrable in a multi-part regimen.

Preferably, the total effective composition is administrable by at least one delivery method selected from the group consisting of: oral delivery and intravenous delivery.

According to the present invention, there is provided for the first time a method for alleviating symptoms associated with premenstrual syndrome (PMS) and premenstrual dysphoric disorder (PMDD) in a subject in need thereof, the method including the step of: (a) administering to the subject an effective amount of a pharmaceutical/nutritional composition including: (i) at least 2% (w/w) phosphatidic acid, or salts thereof, out of a total composition, as an effective ingredient.

Preferably, the pharmaceutical/nutritional composition further includes: (ii) a suitable amount of at least one bio-available form of magnesium as a second effective ingredient.

Most preferably, at least one bio-available form is selected from the group consisting of: magnesium oxide, magnesium citrate, magnesium hydroxide, and magnesium stearate.

Most preferably, at least one bio-available form is a magnesium salt of said phosphatidic acid.

Preferably, the pharmaceutical/nutritional composition further includes: (ii) a pharmaceutical excipient.

Preferably, the pharmaceutical/nutritional composition further includes: (ii) a nutritional excipient.

These and further embodiments will be apparent from the detailed description and examples that follow.

DESCRIPTION OF THE PREFERRED EMBODIMENTS

The present invention relates to compositions and methods for alleviating symptoms associated with PMS and PMDD. The aspects, uses, and advantages for such compositions and methods, according to the present invention, may be better understood with reference to the accompanying description. Exemplary embodiments of the present invention are detailed below in the following exemplary formulations.

Pharmaceutical/nutritional compositions for alleviating symptoms associated with PMS and PMDD were formulated using effective amounts of phosphatidyl-L-serine and at least one bio-available form of magnesium. Some formulations also included phosphatidic acid.

Exemplary Formulation A:

Phosphatidyl-L-serine (PS) was prepared by Lipogen Products (9000) Ltd. via the process of enzymatic reaction from a substrate soybean lecithin using the method described in Example 1-1 of the parent patent application, herein incorporated by reference, by Rutenberg et al. (US Patent Publication No. 2011/0098249, hereinafter referred to as Rutenberg '249) of the present invention. Magnesium oxide (Dr. Paul Lohmann GmbH KG) was used as a bio-available form of magnesium. 250 g. of PS were combined with 250 g. of magnesium oxide to produce the formulation.

Exemplary Formulation B:

PS was prepared by Lipogen Products (9000) Ltd. as in Formulation A. PS was then converted into a magnesium salt by ion exchange with magnesium chloride (Dr. Paul Lohmann GmbH KG). The magnesium salt of PS (PS-Mg) was used as a bio-available form of magnesium. 200 g. of PS-Mg were used to produce the formulation.

Exemplary Formulation C:

PS was prepared by Lipogen Products (9000) Ltd. as in Formulation A. Magnesium citrate (Dr. Paul Lohmann GmbH KG) was used as a bio-available form of magnesium. Phosphatidic acid (PA) was prepared by Lipogen Products (9000) Ltd.). 250 g. of PS were combined with 250 g. of PA and 250 g. of magnesium citrate to produce the formulation.

Exemplary Formulation D:

PS and PA were prepared by Lipogen Products (9000) Ltd. as in Formulation C. PA was then converted into a magnesium salt by ion exchange with magnesium chloride (Dr. Paul Lohmann GmbH KG). The magnesium salt of PA (PA-Mg) was used as a bio-available form of magnesium. 200 g. of PS were combined with 200 g. of PA-Mg to produce the formulation.

Exemplary Formulation E:

PA-Mg was prepared by Lipogen Products (9000) Ltd. as in Formulation D. 200 g. of PA-Mg were used to produce the formulation.

Exemplary Formulation F:

PA was prepared by Lipogen Products (9000) Ltd. as in Formulation C. 500 g. of PA were used to produce the formulation. Magnesium citrate (Dr. Paul Lohmann GmbH KG) was used as a bio-available form of magnesium. 200 g. of PA were combined with 200 g. of magnesium citrate to produce the formulation.

Exemplary Formulation G:

PS was prepared by Lipogen Products (9000) Ltd. as in Formulation A. 500 g. of PS were used to produce the formulation.

Exemplary Formulation H:

PA was prepared by Lipogen Products (9000) Ltd. as in Formulation C. 500 g. of PA were used to produce the formulation.

Results:

The effect of alleviating PMS/PMDD symptoms via oral administration was investigated in the following experiments. In studies involving PS/Mg formulations, the results are presented relative to the studies involving only PS (Formulation G) which were disclosed in Rutenberg '249. In studies involving PA/Mg formulations, the results are presented relative to studies described below involving only PA (Formulation H). It is noted that studies using Formulation H involving PA (Treatment H) showed results comparable to Formulation G involving PS relative to a baseline of no treatment.

The PMS/PMDD symptom scale used was based on an assessment by the subject. Examples of the PMS/PMDD physical symptoms include acne, breast swelling and tenderness, feeling tired, having trouble sleeping, upset stomach, bloating, weight gain, constipation, diarrhea, headache, heart palpitations, backache, appetite changes, food cravings, and joint and muscle pain.

The PMS/PMDD behavioral symptoms include any changes that the subjects noticed in everyday behavior. Examples of the PMS/PMDD behavioral symptoms include feelings of deep sadness or despair, feelings of intense tension or anxiety, increased intense sensitivity to rejection or criticism, panic attacks, rapid and severe mood swings, uncontrollable crying, lasting irritability or anger, apathy, difficulty concentrating, chronic fatigue, severe insomnia or hypersomnia, feeling overwhelmed, feeling out of control, change in sex drive, and increased need for emotional closeness.

Classification of the subjects as suffering from PMDD was based on the presence of five or more of the above symptoms, with the presence of mood symptoms typically being dominant.

The results correlate to the following subjective ranking: "✓"=comparable improvement to PS- or PA-only treatments (Formulations G or H, respectively), "*"=slight improvement above treatments with Formulations G or H, and "**"=large improvement above treatments with Formulations G or H.

Formulation A: Three female volunteers who normally suffer from PMS symptoms and four females who suffer from PMDD received 200 mg. of Formulation A four times per day from three weeks before the expected monthly menstruation until the commencement of menstruation (Treatment A). The results are presented in Table 1. As indicated in Table 1, a significant improvement was observed in all seven participants, irrespective of age and malady of PMS versus PMDD.

TABLE 1

The effect of alleviating PMS/PMDD symptoms using a PS/Mg treatment in an initial treatment-regimen experiment.

| Subject age (suffering from PMS or PMDD) | Physical symptoms with Treatment A | Behavioral symptoms with Treatment A | Cumulative symptoms with Treatment A |
|---|---|---|---|
| 35 (PMS) | * | * | ** |
| 32 (PMS) | * | * | * |
| 34 (PMS) | * | ✓ | * |
| 27 (PMDD) | * | ** | ** |
| 29 (PMDD) | * | ** | ** |
| 28 (PMDD) | * | * | * |
| 32 (PMDD) | * | * | * |

After one menstruation cycles after the menstruation date of the study in Table 1, the same seven females who participated reported that after cessation of the treatment, their usual symptoms reappeared. The above seven female then received 200 mg. of Formulation A four times per day from three weeks before the expected monthly menstruation until the commencement of menstruation (Treatment A). The results are presented in Table 2. As indicated in Table 1, a significant improvement was observed in all seven participants, irrespective of age and malady of PMS versus PMDD.

TABLE 2

The effect of alleviating PMS/PMDD symptoms using a PS/Mg treatment in a secondary treatment-regimen experiment after the re-emergence of symptoms.

| Subject age (suffering from PMS or PMDD) | Physical symptoms with Treatment A | Behavioral symptoms with Treatment A | Cumulative symptoms with Treatment A |
|---|---|---|---|
| 35 (PMS) | * | * | ** |
| 32 (PMS) | * | * | * |
| 34 (PMS) | ** | ✓ | ** |
| 27 (PMDD) | * | ** | ** |
| 29 (PMDD) | * | ** | ** |
| 28 (PMDD) | * | ✓ | * |
| 32 (PMDD) | * | ✓ | * |

Formulation B: Three female volunteers who normally suffer from PMS symptoms and four females who suffer from PMDD received 150 mg. of Formulation B four times per day from three weeks before the expected monthly menstruation until the commencement of menstruation (Treatment B). The results are presented in Table 3. As indicated in Table 3, a significant improvement was observed in all seven participants, irrespective of age and malady of PMS versus PMDD.

TABLE 3

The effect of alleviating PMS/PMDD symptoms using a PS/Mg treatment in an initial treatment-regimen experiment.

| Subject age (suffering from PMS or PMDD) | Physical symptoms with Treatment B | Behavioral symptoms with Treatment B | Cumulative symptoms with Treatment B |
|---|---|---|---|
| 35 (PMS) | * | * | ** |
| 32 (PMS) | ** | * | ** |
| 34 (PMS) | * | ✓ | * |
| 27 (PMDD) | * | ** | ** |
| 29 (PMDD) | ** | ** | ** |
| 28 (PMDD) | * | * | * |
| 32 (PMDD) | * | ** | ** |

Formulation C: Three female volunteers who normally suffer from PMS symptoms and four females who suffer from PMDD received 300 mg. of Formulation C four times per day from three weeks before the expected monthly menstruation until the commencement of menstruation (Treatment C). The results are presented in Table 4. As indicated in Table 4, a significant improvement was observed in all seven participants, irrespective of age and malady of PMS versus PMDD.

TABLE 4

The effect of alleviating PMS/PMDD symptoms using a PS/PA/Mg treatment in an initial treatment-regimen experiment.

| Subject age (suffering from PMS or PMDD) | Physical symptoms with Treatment C | Behavioral symptoms with Treatment C | Cumulative symptoms with Treatment C |
|---|---|---|---|
| 35 (PMS) | ** | * | ** |
| 32 (PMS) | ** | ** | ** |
| 34 (PMS) | ** | ✓ | ** |
| 27 (PMDD) | * | ** | ** |
| 29 (PMDD) | ** | ** | ** |
| 28 (PMDD) | * | ** | * |
| 32 (PMDD) | ** | * | ** |

Formulation D: Three female volunteers who normally suffer from PMS symptoms and four females who suffer from PMDD received 250 mg. of Formulation D four times per day from three weeks before the expected monthly menstruation until the commencement of menstruation (Treatment D). The results are presented in Table 5. As indicated in Table 5, a significant improvement was observed in all seven participants, irrespective of age and malady of PMS versus PMDD.

TABLE 5

The effect of alleviating PMS/PMDD symptoms using a PS/PA/Mg treatment in an initial treatment-regimen experiment.

| Subject age (suffering from PMS or PMDD) | Physical symptoms with Treatment D | Behavioral symptoms with Treatment D | Cumulative symptoms with Treatment D |
|---|---|---|---|
| 35 (PMS) | ** | * | ** |
| 32 (PMS) | ** | * | * |
| 34 (PMS) | * | * | * |
| 27 (PMDD) | ** | ** | ** |
| 29 (PMDD) | * | ** | ** |
| 28 (PMDD) | * | * | * |
| 32 (PMDD) | ** | * | ** |

Formulation E: Three female volunteers who normally suffer from PMS symptoms and four females who suffer from PMDD received 125 mg. of Formulation E four times per day from three weeks before the expected monthly menstruation until the commencement of menstruation (Treatment E). The results are presented in Table 6. As indicated in Table 6, a significant improvement was observed in all seven participants, irrespective of age and malady of PMS versus PMDD.

TABLE 6

The effect of alleviating PMS/PMDD symptoms using a PA/Mg treatment in an initial treatment-regimen experiment.

| Subject age (suffering from PMS or PMDD) | Physical symptoms with Treatment E | Behavioral symptoms with Treatment E | Cumulative symptoms with Treatment E |
|---|---|---|---|
| 35 (PMS) | * | * | ** |
| 32 (PMS) | * | * | * |
| 34 (PMS) | * | ✓ | * |

TABLE 6-continued

The effect of alleviating PMS/PMDD symptoms using a PA/Mg
treatment in an initial treatment-regimen experiment.

| Subject age (suffering from PMS or PMDD) | Physical symptoms with Treatment E | Behavioral symptoms with Treatment E | Cumulative symptoms with Treatment E |
|---|---|---|---|
| 27 (PMDD) | * | * | * |
| 29 (PMDD) | * | ** | ** |
| 28 (PMDD) | ** | * | ** |
| 32 (PMDD) | * | * | * |

Formulation F: Three female volunteers who normally suffer from PMS symptoms and four females who suffer from PMDD received 200 mg. of Formulation F four times per day from three weeks before the expected monthly menstruation until the commencement of menstruation (Treatment F). The results are presented in Table 7. As indicated in Table 7, a significant improvement was observed in all seven participants, irrespective of age and malady of PMS versus PMDD.

TABLE 7

The effect of alleviating PMS/PMDD symptoms using a PA/Mg
treatment in an initial treatment regimen experiment.

| Subject age (suffering from PMS or PMDD) | Physical symptoms with Treatment F | Behavioral symptoms with Treatment F | Cumulative symptoms with Treatment F |
|---|---|---|---|
| 35 (PMS) | * | * | * |
| 32 (PMS) | ** | * | ** |
| 34 (PMS) | * | ✓ | * |
| 27 (PMDD) | * | ** | ** |
| 29 (PMDD) | * | ** | ** |
| 28 (PMDD) | ** | * | ** |
| 32 (PMDD) | * | * | * |

The treatments can be continuously and readily administered with no pain because the PS, PA, and Mg supplied in the compositions described above are freely ingested.

While the present invention has been described with respect to a limited number of embodiments, it will be appreciated that many variations, modifications, and other applications of the present invention may be made.

What is claimed is:

1. A method for alleviating symptoms associated with premenstrual syndrome (PMS) and premenstrual dysphoric disorder (PMDD) in a subject in need thereof, the method comprising the step of:
   (a) administering to the subject an effective amount of a pharmaceutical/nutritional composition including:
      (i) at least 2% (w/w) phosphatidic acid, or salts thereof, out of a total composition, as an effective ingredient.

2. The method of claim 1, wherein said pharmaceutical/nutritional composition further includes:
   (ii) a suitable amount of at least one bio-available form of magnesium as a second effective ingredient.

3. The method of claim 2, wherein said at least one bio-available form is selected from the group consisting of: magnesium oxide, magnesium citrate, magnesium hydroxide, and magnesium stearate.

4. The method of claim 2, wherein said at least one bio-available form is a magnesium salt of said phosphatidic acid.

5. The method of claim 1, wherein said pharmaceutical/nutritional composition further includes:
   (ii) a pharmaceutical excipient.

6. The method of claim 1, said pharmaceutical/nutritional composition further includes:
   (ii) a nutritional excipient.

* * * * *